United States Patent [19]

Kessler

[11] 3,986,962

[45] Oct. 19, 1976

[54] NOVEL ASSEMBLY FOR SEPARATING BLOOD

[75] Inventor: Stephen B. Kessler, Guttenberg, N.J.

[73] Assignee: Becton, Dickinson and Company, East Rutherford, N.J.

[22] Filed: July 10, 1975

[21] Appl. No.: 594,711

[52] U.S. Cl. ........................... 210/516; 210/DIG. 23
[51] Int. Cl.² .................................. B01D 21/26
[58] Field of Search .............. 23/230 B, 258.5, 259, 23/292; 128/2 F, 214 R, 218 M, 272.1, 272, 272.3; 206/219, 221, 222; 210/83, 84, 514–518, DIG. 23, DIG. 24; 215/DIG. 8; 233/1 A, 1 R, 26

[56] References Cited
UNITED STATES PATENTS

| | | | |
|---|---|---|---|
| 2,584,397 | 2/1952 | Pitman | 128/272.3 |
| 2,608,972 | 9/1952 | Chrigstrom | 128/272 |
| 2,812,231 | 11/1957 | Zar | 210/DIG. 23 |
| 3,139,121 | 6/1964 | Ballin | 215/DIG. 8 |
| 3,608,550 | 9/1971 | Stawski | 128/272.3 |
| 3,780,935 | 12/1973 | Lukacs et al. | 210/83 X |
| 3,852,194 | 12/1974 | Zine, Jr. | 210/DIG. 23 |
| 3,901,219 | 8/1975 | Kay | 128/2 F |
| 3,920,557 | 11/1975 | Atres | 210/DIG. 23 |

FOREIGN PATENTS OR APPLICATIONS 399,702    10/1933    United Kingdom ................ 128/272

Primary Examiner—Charles N. Hart
Assistant Examiner—Robert G. Mukai
Attorney, Agent, or Firm—Kane, Dalsimer, Kane, Sullivan and Kurucz

[57] ABSTRACT

Disclosure is made of an improved assembly for the collection, separation and isolation of serum or plasma from blood without subjecting the desired serum or plasma to contamination by exposure to the atmosphere and which utilizes a thixotropic barrier material to effect the isolation. A representative embodiment of the improved assembly comprises an air-evacuated collection chamber, a self-sealing airtight elastomeric closure for the container which is penetrable by a blood bearing cannula and a thixotrope having a specific gravity of from about 1.03 to about 1.09, held in a specially constructed reservoir positioned within the closure member and in communication with the air-evacuated chamber.

4 Claims, 3 Drawing Figures

NOVEL ASSEMBLY FOR SEPARATING BLOOD

BACKGROUND OF THE INVENTION

1. Field of the Invention

The invention concerns the centrifugal separation of blood into its component parts of serum or plasma and cellular material and more specifically concerns an assembly for the collection, separation and isolation of serum or plasma from blood by the application of centrifugal force.

2. Brief Description of the Prior Art

Prior hereto apparatus for isolating blood serum from whole blood by centrifugation of the blood in the presence of a thixotropic sealant barrier was disclosed in U.S. Pat. No. 3,780,935. U.S. Pat. No. 3,852,194 discloses apparatus for isolating blood serum from whole blood by centrifugation to emplace a thixotropic sealant barrier. In the latter disclosure the assembly comprises an air-evacuated blood collection chamber within which there is loosely disposed a thixotrope. In such an assembly there is a tendency for the loose thixotrope to coat the inner walls of the blood collection container. This coating prevents the subsequently collected blood from contacting the glass walls. Contact between the collected blood and the glass is desirable to facilitate the rapid clotting of the blood, prior to centrifugation.

The assembly of my invention is an improvement over the prior art. For example, the assembly of my invention permits one to use a thixotrope sealant to isolate the serum or plasma from blood without prolonging clot formation of the collected whole blood. The assembly of my invention is economical to construct and does not require extensive training to operate.

SUMMARY OF THE INVENTION

The invention comprises an assembly for the collection, separation and isolation of serum or plasma from blood which comprises; a tubular container having an open end and which defines a blood collection chamber; a self-sealing, cannula penetrable, elastomeric closure member hermetically sealing said open end; a recess in the inner surface of said closure member; a thixotrope barrier dispenser secured in said recess, said dispenser comprising (A) a tubular body having an open lower end and which defines a thixotrope reservoir; and (B) a conduit passing through the center of said reservoir and providing communication between the adjacent closure member and the blood collection chamber; and a thixotrope sealant disposed in said reservoir, said thixotrope having a specific gravity within the range of from about 1.03 to about 1.09; said assembly being air-evacuated to provide at least a partial vacuum in said blood collection chamber.

The assembly of the invention is useful to protect the desired serum or plasma from contamination by airborne contaminants such as, for example, lead compounds, airborne bacteria, nitrogen oxides and the like which would adversely affect certain diagnostic tests.

DETAILED DESCRIPTION OF THE INVENTION

Figure 1:
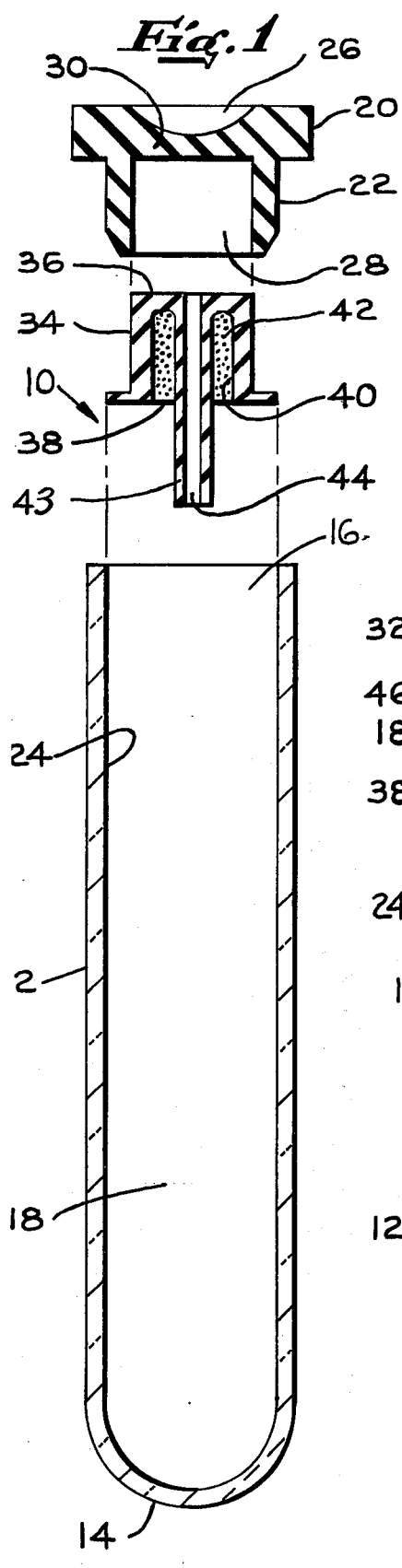
FIG. 1 is a cross-sectional side elevation of a preferred embodiment of the invention shown with the components separated.
Figure 2:
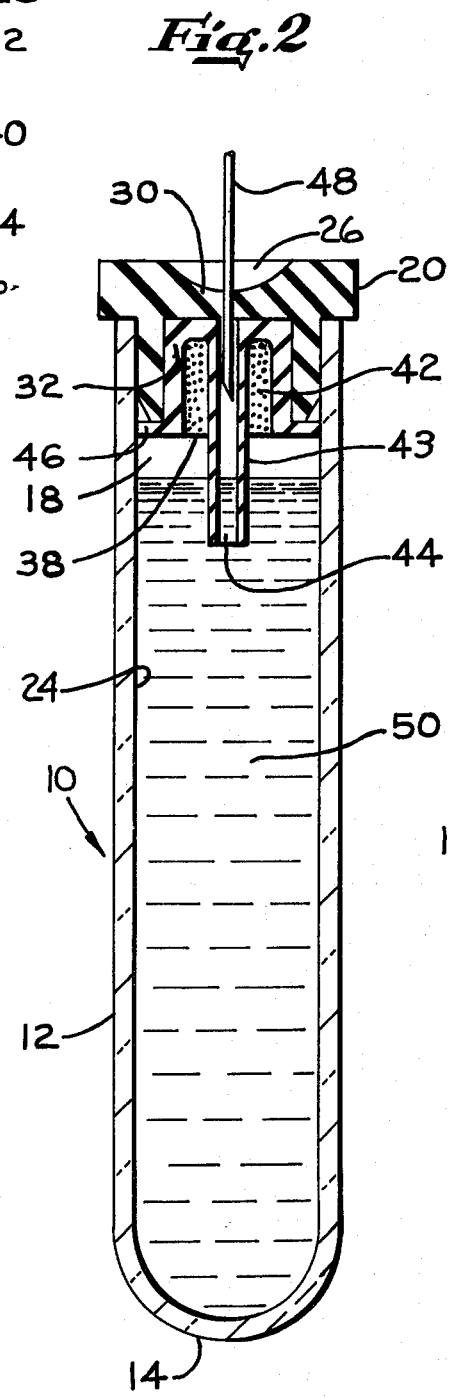
FIG. 2 is a cross-sectional side elevation of the assembly shown in FIG. 1 but with components in place and with blood filling the blood collection chamber.
Figure 3:
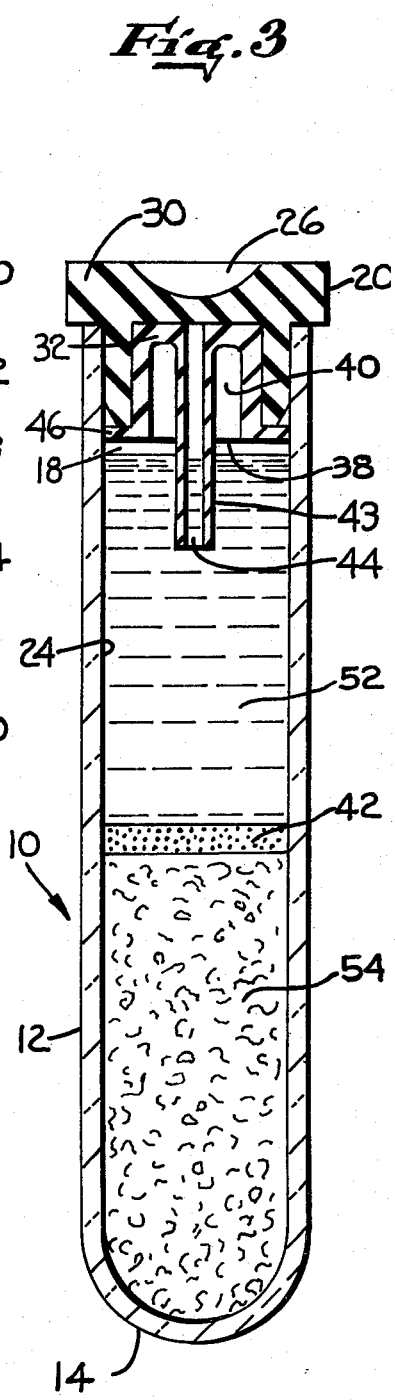
FIG. 3 is a cross-sectional side elevation as shown in FIG. 2 but following centrifugation to effect separation of the blood into its component parts.

A complete understanding of the invention may be readily obtained by referring to the illustrative embodiments shown in the accompanying drawings of FIGS. 1–3, inclusive.

FIG. 1 is a cross-sectional side elevation of a preferred embodiment of the invention shown with the components separated. Thus, there is shown an assembly 10 which consists of a glass tubular container 12 having a closed end 14 and an open end 16. The glass tubular container 12 together with its ends defines a blood collection chamber 18. The open end 16 of assembly 10 is closed with a self-sealing, air tight, elastomeric closure 20 which comprises a plug having sidewalls 22 for engaging the inner walls 24 of glass tubular container 12 in an air tight, hermetic seal. The closure 20 has a recess 26 in the upper surface thereof and a deep axial recess 28 in the bottom surface thereof. Separating recesses 26 and 28 is a thin cannula penetrable zone 30. A thixotrope dispenser 32 is shown to consist of a tubular body 34 having a closed upper end 36 and a lower open end 38. The tubular body 34 together with ends 36 and 38 defines a thixotrope reservoir chamber 40 which is shown filled with thixotrope 42. Traversing the entire dispenser 32 through its center is a conduit 43 providing an open passageway 44 traversing the entire dispenser 32. Thixotrope dispenser 32 is preferably constructed of a hemorepellant, i.e.; a material which will discourage attachment or collection of cellular blood materials. Illustrative of hemorepellant materials are polyethylene, polypropylene, polybutadiene and the like. This preferred material for the dispenser 32 prevents cellular material in the blood from attaching itself to the closure member 20 which is in effect walled off from blood collection chamber 18 by the structure of dispenser 32.

As shown more clearly in FIG. 2, thixotrope dispenser 32 is adapted to fit into recess 28 of closure member 20. The thixotrope dispenser 32 is secured in place by any convenient and conventional means. For example dispenser 32 may be secured in recess 28 with an adhesive or by a tight frictional fit. FIG. 2 also clearly shows that the dispenser 32 including peripheral flanges 46 isolate closure 20 from blood collection chamber 18. The assembly 10 is provided with chamber 18 initially at least partially air-evacuated so there is at least a partial vacuum in chamber 18.

The assembly of FIGS. 1 and 2 is operated as follows. As shown in FIG. 2, a blood bearing cannula 48 has been introduced through thin cannula penetrable zone 30 of closure 20 and traverses passageway 44 of conduit 43. Cannula 48 is attached by conventional blood transfer apparatus (not shown) to a source of blood. The partial vacuum provided within the blood collection chamber 18 draws the blood from blood bearing cannula 48 into the collection chamber 18. If plasma is desired, the chamber 18 may be precharged with anti-coagulant so the whole blood drawn admixes with the anti-coagulant upon being drawn into chamber 18. Upon filling blood collection chamber 18 the blood bearing cannula 48 is withdrawn whereupon the self-sealing elastomeric closure seals itself. As shown in FIG. 2 blood collection chamber 18 has been filled with blood 50 and is now ready for separation by centrifugation. After filling, if serum is desired, the blood 50 is allowed to stand so a clot is formed of most of the cellular materials. The clotting mechanism is aided by contact of the blood 50 with the glass walls of the chamber 18. The blood filled assembly 10 is centrifuged in a conventional manner to effect separation of the blood 50 into its component light plasma or serum 52 and its heavy substantially cellular portion 54. Referring now to FIG. 3, a cross-sectional side elevation as seen in FIG. 2 but following centrifugation to effect separation of blood 50 into its component parts, there is seen assembly 10 containing the separated serum or plasma 52 and the substantially cellular portion 54 of the blood. As seen in FIG. 3, the centrifugal force has also carried the thixotrope 42 out of its reservoir 40 and caused its emplacement (due to its selected density) at the interface between the separated blood components 52 and 54 where it forms a rigid barrier seal. Thixotrope 42 is a gel-like material, preferably hydrophobic, which is a thixotrope. Preferably the thixotropic material is inert to reaction with blood, blood components or reagents commonly employed in diagnostic procedures upon blood. The thixotrope material will have a specific gravity within the range of from about 1.03 to about 1.09, preferably 1.06. This range of specific gravity enables the thixotropic material to flow under centrifugal force to its density gradient layer between blood serum or plasma (having a specific gravity of circa 1.03) and the substantially cellular portion of the blood (which has a specific gravity of circa 1.09).

Thixotropic materials 42 commonly employed to form sealed barriers between the density separated components of blood are well known in the art and need not be described in detail herein. For example, thixotropic sealant barrier materials which may be employed are illustrated by silicone oils thickened with fumed silicon dioxide; see the disclosures of U.S. Pat. Nos. 3,780,935 and 3,852,194 for further description of thixotropic sealant materials which may be employed as barriers to separate and isolate blood serum or plasma from the substantially cellular portion of blood. Preferred thixotrope 42 sealant materials have a viscosity of at least about 30,000 centistokes so that they may adhere and be retained within reservoir 40 under the force of one gravity. Alternatively, lower viscosity thixotropic 42 materials may be employed provided the openings 38 of reservoir 40 are of a dimension such that the thixotrope 42 will not flow out under the force of one garvity but will flow through openings 38 under increased centrifugal force. Those skilled in the art will appreciate the relationship between thixotropy and the dimensions of openings 38 and will understand how to select a proper degree of thixotropy using trial and error techniques. Those skilled in the art will appreciate that the opening 38 may be varied in dimension according to the exact thixotropy of the thixotrope 42 selected.

After separation and isolation of the desired blood serum or plasma, the assembly 10 may be handled, mailed, etc., without remixing with the cellular component. When desired, the closure 20 may be removed to gain access to the serum or plasma 52. Alternatively, to continue protecting the serum or plasma 52 from exposure to the atmosphere, a syringe may be used to penetrate closure 20 to withdraw the serum or plasma 52.

Those skilled in the art will also appreciate that one may vary the embodiment described above considerably without departing from the spirit and the scope of the invention set forth in the following claims. For example, the tubular container 12 may have more than one opening so long as each opening is hermetically sealed.

What is claimed:

1. An assembly for the collection, separation and isolation of serum or plasma from blood, which comprises;
   a. a tubular container having an open end and which defines a blood collection chamber;
   b. a self-sealing, cannula-penetrable, elastomeric closure member hermetically sealing said open end;
   c. a recess in the inner surface of said closure member;
   d. a thixotrope barrier dispenser secured in said recess, said dispenser comprising;
      i. a tubular body fabricated of hemorepellant material and having an open lower end which defines a thixotrope reservoir, said open lower end being insufficient in size to permit pasage of said thixotrope under the force of one gravity but of sufficient size to permit passage of said thixotrope when the thixotrope is subjected to a centrifugal force in substantial excess of one gravity; and
      ii. a conduit passing through the center of said reservoir and providing communication between the adjacent closure member and the blood collection chamber said conduit extending partially into said blood collection chamber; and
   e. a thixotrope sealant disposed in said reservoir, said thixotrope having a specific gravity within the range of from about 1.03 to about 1.09; said assembly being air-evacuated to provide at least a partial vacuum in said blood collection chamber.

2. The assembly of claim 1 wherein said container is glass.

3. The assembly of claim 1 wherein said thixotrope has a specific gravity of 1.06.

4. The assembly of claim 1 wherein said thixotrope has a viscosity of at least about 30,000 centistokes.

* * * * *